United States Patent [19]

Golay

[11] Patent Number: 4,995,163

[45] Date of Patent: Feb. 26, 1991

[54] METHOD OF ASSEMBLING A CHROMATOGRAPHY COLUMN

[75] Inventor: Marcel Golay, La Conversion, Switzerland

[73] Assignee: The Perkin-Elmer Corporation, Norwalk, Conn.

[21] Appl. No.: 398,676

[22] Filed: Aug. 25, 1989

Related U.S. Application Data

[62] Division of Ser. No. 41,554, Apr. 22, 1987, Pat. No. 4,872,979.

[51] Int. Cl.$^5$ ................ B23P 19/04; B23P 25/00
[52] U.S. Cl. ................ 29/527.1; 29/33 F; 29/419.1; 29/461; 264/258
[58] Field of Search ........ 29/33 F, 419.1, 445, 29/446, 452, 461, 464, 467, 527.2; 57/3, 6, 293, 295; 264/258; 156/51, 52, 172, 173, 195; 210/198.2, 198.3, 502.1, 321.87, 497.1, 635, 656

[56] References Cited

U.S. PATENT DOCUMENTS

| | | | |
|---|---|---|---|
| 3,728,425 | 4/1973 | Schrader | 264/258 X |
| 4,023,835 | 5/1977 | Ewing et al. | 156/173 X |
| 4,048,075 | 9/1977 | Colvin et al. | 427/244 X |
| 4,157,181 | 6/1979 | Cecka | 156/195 X |
| 4,266,399 | 5/1981 | Ellis, Jr. | 57/293 |
| 4,309,865 | 1/1982 | Brunsch et al. | 57/295 |
| 4,446,689 | 5/1984 | Hardin et al. | 57/293 X |
| 4,631,128 | 12/1986 | Coplan et al. | 210/321.87 |
| 4,675,104 | 6/1987 | Rai et al. | 210/198.2 |

Primary Examiner—Joseph M. Gorski
Assistant Examiner—Peter Dungba Vo
Attorney, Agent, or Firm—Thomas P. Murphy; Edwin T. Grimes

[57] ABSTRACT

Disclosed is a method of assembling a chromatography column including the steps of providing a cylindrical core element, winding an innermost layer of uniformly spaced fibers helically about the core element, winding a plurality of concentric annular layers of uniformly spaced fibers about the innermost layer so that the fibers of each layer are helically wound about the most inwardly adjacent layer in reverse hand orientation relative to the next inwardly adjacent layer, enveloping the outermost layer of fibers in a column housing, and coating the fibers with stationary phase material.

10 Claims, 1 Drawing Sheet

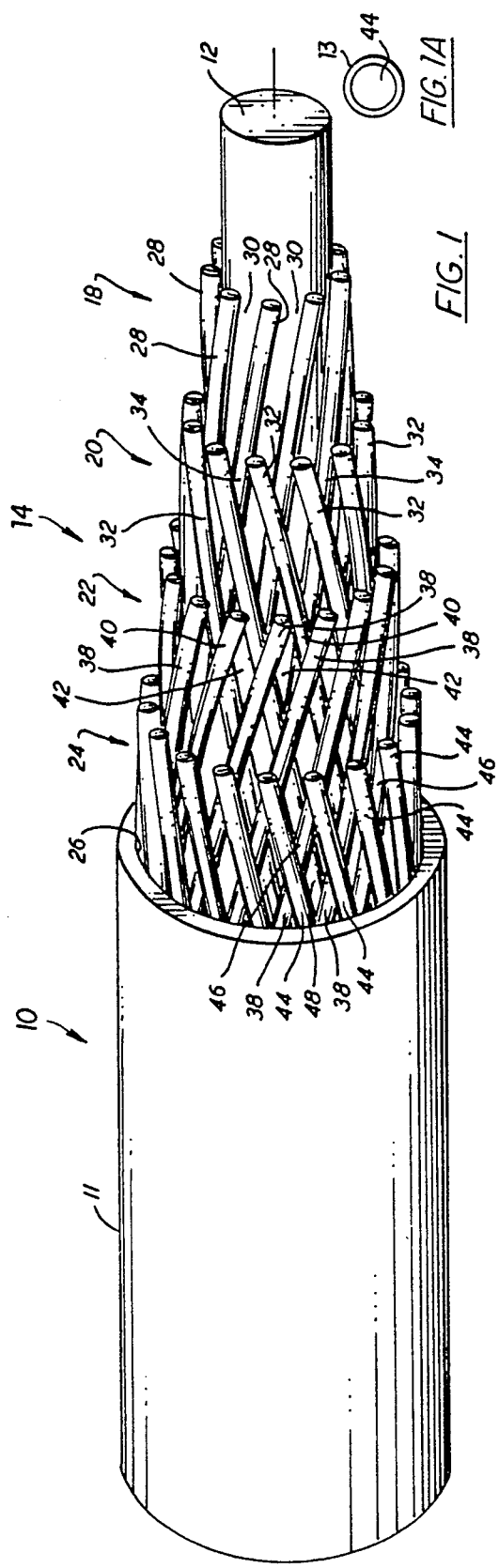
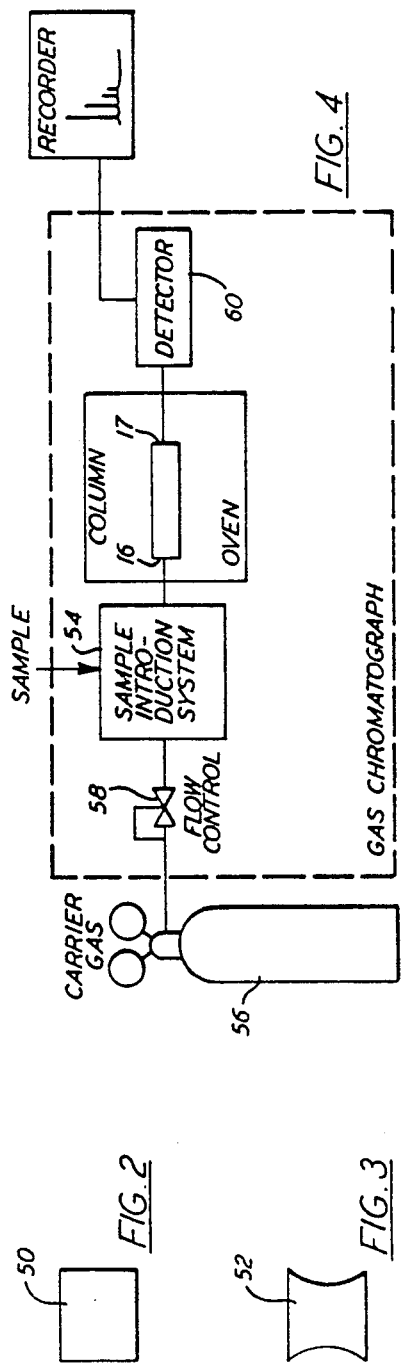

METHOD OF ASSEMBLING A CHROMATOGRAPHY COLUMN

This application is a division of application Ser. No. 07/041,554, filed 4/22/87 now U.S. Pat. No. 4,872,979.

BACKGROUND AND SUMMARY OF THE INVENTION

This invention relates to chromatography and more particularly to chromatographic columns having particular utility in preparative gas chromatography.

Previously, there have been essentially two formats of gas chromatographic columns. The more efficient format is that of an open tubular column with the walls coated with the stationary or fixed phase material. This format, sometimes referred to as a Golay or capillary column, is used for chemical analysis in which small samples are sufficient.

When the output of a capillary column is not sufficient for the desired analysis or when larger outputs are required for further chemical processes as in preparative scale chromatography, the preferred format has been that of a tube packed with porous particles or granules impregnated or coated with the fixed phase material. This format, generally referred to as a packed column, has the advantage of relatively large throughput, but is slower and less efficient. Typically, with equal pressures being applied at the inlet of the columns, a separation requiring one minute with a capillary column will require several hours with a packed column.

The poor efficiency of the packed column is explainable by certain nonuniformity characteristics of this format. Firstly, there is the circumstance that any one rivulet of gas snaking its way among the packing granules alternately encounters very narrow passages between three contacting granules which offer high resistance to flow and large passages which require relatively long times for the sample molecules to diffuse to and from the fixed phase which is coated on the walls of these larger passages. In contrast, the single passage of a capillary column is of uniform dimension and this single dimension determines both the resistance to flow and the diffusion time to and from the wall. Secondly, there is the circumstance that the various rivulets of gas which may have a common origin and which meet again further along the column may have required appreciably different times for their separate travels. These travel time differences cause an unwanted spread of the various separated components in space along the column and eventually in time at the column exit and consequently the components may merge into each other instead of being clearly separated. Thus, there are some undesirable attributes of lengthwise and crosswise nonuniformity of the column.

From time to time there have been suggestions to provide a column of higher throughput and high timewise efficiency by manifolding a number of like capillary working in parallel as a single column. However, this suggestion has not been successful. Firstly, such a column would be cost prohibitive, e.g., the cost of one hundred capillary columns would be prohibitive. Secondly, the task of trimming such a large number of columns so that they would have the same time of passage for all the components of a given sample would be practically hopeless.

Accordingly, it is an object of the present invention to provide a new and improved chromatographic column.

Another object of the invention is to provide a chromatographic column having high efficiency and relatively large throughput suitable for preparative scale chromatography.

A further object of the invention is to provide a chromatographic column having multiple uniform passageways with crosswise communication for attaining uniform frontal distribution of separated components. Included in this objective is the provision of passageways having a high degree of lengthwise and crosswise uniformity.

A still further object of the invention is to provide such a chromatographic column which is economical to manufacture and efficient in operation.

A still further object of the invention is to provide a new and improved technique for forming a chromatographic column which is economical and efficient.

Other objects will be in part obvious and will be in part pointed out more in detail hereinafter.

Accordingly, it has been found that the foregoing and related objectives and advantages can be obtained in a chromatographic column comprising a housing having an inlet and an outlet end and a plurality of uniform fluid passageways extending axially within the housing between the inlet and outlet ends. The passageways are coated with a stationary phase material and lateral openings disposed longitudinally along the passageways laterally interconnect adjacent passageways to permit fluid communication and/or molecular diffusion therebetween. In a preferred embodiment of the invention, the plurality of the fluid passageways are formed by a configuration of fiber layers disposed about an elongated central core element extending longitudinally within the housing. The fiber layer configuration comprises an innermost layer having a plurality of fibers helically wound about the central element with the fibers being in predetermined spaced disposition for forming a fluid passageway between adjacent fibers. A plurality of outwardly successive fiber layers are disposed about the innermost layer with each successive layer having a plurality of fibers helically wound in reverse hand relative to the previous adjacent layer and in predetermined space disposition for forming a fluid passageway between adjacent fibers with a plurality of lateral openings fluidly cross-connecting overlapping longitudinal fluid passageways.

BRIEF DESCRIPTION OF THE DRAWINGS

FIG. 1 is a partly broken away perspective view of a chromatographic column according to the present invention.

FIG. 1A illustrates an end view of a fiber of a layer with the stationary phase material coated thereon.

FIG. 2 is a cross-sectional view of an alternate fiber element.

FIG. 3 is a cross-sectional view of another alternate fiber element.

FIG. 4 is a schematic diagram of a gas chromatography system including the column of the present invention.

DESCRIPTION OF THE PREFERRED EMBODIMENT

Although specific forms of the present invention have been selected for illustration in the drawings, and the following description is drawn in specific terms for the purpose of describing these forms of the invention, the description is not intended to limit the scope of the invention which is defined in the appended claims.

Referring to FIG. 1, the chromatography column of the present invention is designated by the numeral 10 and generally comprises an elongated column housing 11, an elongated central core element 12, a configuration of fibers, generally designated by the numeral 14, disposed about the core element 12 so as to form a plurality of fluid passageways through the housing 11, and a coating 13 of stationary phase material on the passageways.

The core element 12 is a cylindrical fiber extending coaxially within the cylindrical housing 10 between the inlet end 16 and outlet end 17 of the housing. The fiber configuration 14 comprises a plurality of annular, concentric, wound fiber layers 18, 20, 22, 24 extending between the core fiber 12 and the inner wall 26 of the cylindrical housing 11.

The innermost fiber layer 18 is formed by a plurality of uniformly spaced cylindrical fibers 28 helically wound about the core fiber 12. The spaces 30 between the fibers 28 form uniform parallel fluid passageways being bound on the inner side by the core element 12 and on the opposing outer side by the adjacent fiber layer 20. The fiber layer 20 is similarly formed by a plurality of uniformly spaced cylindrical fibers 32 helically wound about the innermost layer 18 in reverse hand relative to the fibers 28 of layer 18. The spaces 34 between adjacent fibers 32 form parallel uniform passageways bound on the inner side by the next innermost adjoining layer 18 and bound on the outer side by the next outermost adjoining layer 22.

In the illustrated embodiment, the helically wound fibers 28 of the innermost layer 18 are right hand wound so that the passageways 30 follow identical right hand helical paths about the core fiber 12 between the inlet end 16 and the outlet end 17 of the housing 11. Conversely, the passageways 34 formed by the left hand helically wound fibers 32 follow a left hand helical path about the inner layer 18 between the inlet and outlet ends of the housing 11. Consequently, the left hand oriented passageways 34 cross over the right hand oriented passageways 30 so that common uniform lateral openings 36 are formed between the passageways 30, 34 where the passageways 34 adjoin the passageways 30 to thereby fluidly interconnect the overlapping fluid passageways at a plurality of locations longitudinally along the passageways.

Similarly, the fibers 38 of layer 22 are uniformly spaced and helically wound in right hand orientation about the layer 20. The spaces 40 between the fibers 38 form uniform fluid passageways being bound on one side by the next inwardly adjacent fiber layer 20 and being bound on the opposite side by the next outwardly adjacent fiber layer 24. The passageways 40 follow a right hand oriented helical path about the layer 20 and therefore crossover the left hand helical passageways 34 of layer 20. Common uniform lateral openings 42 are formed between the passageways 40, 34 where the passageways 40 adjoin the passageways 34 to thereby fluidly interconnect the overlapping passageways longitudinally along the passageways between the inlet and outlet ends of the housing.

The outermost fiber layer 24 is similarly formed by a plurality of uniformly spaced cylindrical fibers 44 helically wound in left hand orientation about the fiber layer 22. The spaces 46 between the fibers 44 form passageways bounded on the outer side by the inner wall 26 of housing 10 and on the inner side by the fiber layer 22. The housing 11 is in close fitting disposition about the annular layer 24.

The left hand helical passageways 46 of layer 24 cross over the right hand helical passageways 40 of layer 22 so that common uniform lateral openings 48 are formed between the passageways 46, 40 where the passageways 46 adjoin the passageways 40 to thereby fluidly and/or diffusively interconnect the overlapping fluid passageways at a plurality of locations longitudinally along the passageways. Overall, the uniform lateral openings disposed longitudinally along the column 10 provide for cross-communication or crossdiffusion of carrier gas and sample for equilibrium between the passageways for the entire column.

The fibers 28, 32, 38, 44 are of equal diametrical size being typically 0.008 inch diameter titanium wire. The core fiber 12 has a diametrical size typically 5 times the size of the other fibers, being thus approximately 0.04 inch diameter titanium wire. Alternately, a core element of another dimension may be used, such as a fiber similar to those used in the fiber layers.

In the typical configuration shown, the innermost layer 18 has 9 fibers and each radially outwardly successive fiber layer increases by three fibers, i.e., fiber layer 20 has 12 fibers, fiber layer 22 has 15 fibers, and fiber layer 24 has 18 fibers. As can be appreciated, the number of uniform passageways formed by each fiber layer is equal to the number of fibers in the respective layer.

The fibers 32, 38 of the intermediate layers 20, 22 are equi-spaced by approximately their diametrical size, i.e., 0.008 inches. The climbing angles of the helically wound fibers of the intermediate layers 20, 22 are equal being approximately 20°. Since the fluid velocity through the passageways 46 of the outermost layer 24 is slowed by the influence of the adjacent inner wall 26 of housing 11, the climbing angle of this outermost layer is steeper so that the distance between the adjacent fibers 44 is greater than the diameter of the fibers; also, the path lengths along this outer layer will also be shorter than the neighboring inner layer, all for the purpose of attaining uniform frontal distribution of the sample elements. A similar compensation is likewise required for the innermost layer 18 because of the influence of the adjoining core fiber 12, i.e., a steeper climbing angle. In the illustrated embodiment, the climbing angles of the fibers 28 and 44 are 10°.

Although only two intermediate fiber layers 20, 22 have been shown in the illustrated embodiment, it is understood that any suitable plurality of such intermediate layers may be utilized depending upon the output desired with the fibers of each successive fiber layer being helically wound in reverse hand relative to the next adjacent layer and with the intermediate layers having equal climbing angles.

The cylindrical housing 11 closely envelopes the outermost fiber layer and withstands the input pressure of the conventional chromatographic process. A suitable housing can be formed of TEFLON and heat shrunk by conventional methods to frictionally retain the fibers in the wound fiber configuration.

The passageways 30, 34, 40, 46 formed by the respective fibers 28, 32, 38, 44 are coated with a conventional stationary phase material such as CARBOWAX. For purposes of explanation, FIG. 1A shows only one of the fibers 44 of layer 24 with the coating 13 thereon. Such coating is accomplished by coating the fibers prior to assembly or, alternately, after assembly.

Titanium wire is the preferred material for the fiber elements although other metal wires such as aluminum provide acceptable results. Alternately, the fibers may be made of glass or glass-like substances such as fused silica.

Alternate fiber forms may be utilized for the wound fiber layers. A square fiber 50, such as shown in cross-section in FIG. 2, may be utilized as well as a fiber 52 being quadrilateral in cross-section with a pair of opposed incurvated sides as shown in FIG. 3. The intended advantage of the quadrilateral configuration is to avoid narrow corners that would constitute a stream holdup.

In operation, the column 10 of the present invention is utilized in a conventional system which is schematically illustrated in FIG. 4 and need not be described in great detail. As shown in FIG. 4, the inlet end 16 of the column is connected to the sample introduction system 54. A source of carrier gas 56 is interconnected to the sample introduction system 54 by a flow control regulator 58. A conventional detector 60 is connected to the outlet end 17 of the column 10.

The method of forming or assembling the column of the present invention includes maintaining the core element in a linear disposition and helically winding a plurality of wire elements about the core element in uniform predetermined spaced disposition at a predetermined climbing angle as previously explained. A second layer is formed by helically winding a plurality of fiber elements in opposite hand about the first layer in predetermined spaced disposition and at a predetermined climbing angle as previously explained. Successive fiber layers are similarly formed each being wound in reverse hand relative to the previous adjacent layer. When the desired number of layers have been appropriately wound, the column housing is mounted about the fiber configuration. The housing is formed of TEFLON and heat shrunk by conventional methods to frictionally retain the fiber configuration. The passageways formed by the fiber layers are coated with a stationary phase material by coating the fiber elements defining the passageways. The fiber elements are coated prior to winding or, alternately, after winding.

As can be seen, a chromatographic column is provided which achieves a high degree of lengthwise and crosswise uniformity as well as crosswise diffusion for attaining uniform frontal distribution of all components of a sample. The column has high efficiency and relatively large throughput suitable for preparative scale chromatography and is economical to manufacture and efficient in operation.

As will be apparent to persons skilled in the art, various modifications and adaptations of the structure and method above described will become readily apparent without departure from the spirit and scope of the invention, the scope of which is defined in the appended claims.

I claim:

1. A method of assembling a chromatography column comprising the steps of; providing a cylindrical core element, forming plural layers of fibers onto said core element, each of said layers having plural fluid passageways, each of said passageways is defined by a space existing between every two adjacent fibers, wherein the step of forming the layers comprises, winding an innermost layer of uniformly spaced fibers helically about the core element, winding a plurality of concentric annular layers of uniformly spaced fibers about the innermost layer so that the fibers of each layer are helically wound about the next inwardly adjacent layer in reverse hand orientation relative to the next inwardly adjacent layer, enveloping the outermost layer of fibers in a column housing, and coating the fibers with stationary phase material.

2. The method of claim 1 including performing the coating step after the step of winding a plurality of concentric annular layers.

3. The method of claim 1 including performing the coating step prior to the step of winding a plurality of concentric layers.

4. The method of claim 1 wherein the windings of fibers form a fiber configuration and the step of enveloping the outermost layer of fibers comprises mounting the fiber configuration in a close-fitting housing thereby frictionally retaining the fiber configuration.

5. The method of claim 1 including the step of winding the fibers of the intermediate layers between the innermost and outermost layers at equal climbing angles.

6. The method of claim 5 including the step of winding the fibers of the outermost layer at a steeper climbing angle than the climbing angle at which the intermediate layers are wound.

7. The method of claim 5 including the step of winding the fibers of the innermost layer at a steeper climbing angle than the climbing angle at which the intermediate layers are wound.

8. The method of claim 1 including the step of winding the fibers of the intermediate layers between the innermost and outermost layers to be equi-spaced a first predetermined distance.

9. The method of claim 8 including the step of winding the fibers of the outermost layer to be equi-spaced a second predetermined distance greater than said first predetermined distance.

10. The method of claim 8 including the step of winding the fibers of the innermost layer to be equi-spaced a second predetermined distance greater than said first predetermined distance.

* * * * *